(12) United States Patent
Hirano et al.

(10) Patent No.: US 7,449,151 B2
(45) Date of Patent: Nov. 11, 2008

(54) FLUORESCENCE RESONANCE ENERGY TRANSFER ANALYZER

(75) Inventors: Masahiko Hirano, Hamamatsu (JP); Masafumi Oshiro, Hamamatsu (JP); Atsushi Miyawaki, Wako (JP)

(73) Assignees: Riken, Wako-shi, Saitama (JP); Hamamatsu Photonics K.K., Hamamatsu-shi, Shizuoka (JP)

( * ) Notice: Subject to any disclaimer, the term of this patent is extended or adjusted under 35 U.S.C. 154(b) by 1032 days.

(21) Appl. No.: 10/753,569

(22) Filed: Jan. 9, 2004

(65) Prior Publication Data

US 2004/0146913 A1 Jul. 29, 2004

(30) Foreign Application Priority Data

Jan. 9, 2003 (JP) ............................ P2003-003450

(51) Int. Cl.
G01N 33/00 (2006.01)
(52) U.S. Cl. ................ 422/82.08; 422/68.1; 422/82.05; 422/82.09; 436/164; 436/172
(58) Field of Classification Search .............. 422/82.08, 422/55, 68.1, 82.09, 82.05; 436/164, 172
See application file for complete search history.

(56) References Cited

U.S. PATENT DOCUMENTS

| 4,900,934 | A | 2/1990 | Peeters et al. ............ 250/461.2 |
| 5,866,355 | A | 2/1999 | Miyakawa et al. ............ 435/29 |
| 6,396,053 | B1 | 5/2002 | Yokoi ........................ 250/234 |
| 2001/0012152 | A1 | 8/2001 | Satou ........................ 359/385 |
| 2002/0085293 | A1 | 7/2002 | Stuckey ...................... 359/831 |

OTHER PUBLICATIONS

Miyawaki et al.; "Fluorescent Indicators for Ca$^{2+}$ Based on Green Fluorescent Proteins and Calmodulin"; Nature, vol. 388, (Aug. 1997); pp. 882-887.
Sawano et al.; "Multicolor Imaging for Ca$^{2+}$ and Protein Kinase C Signals Using Novel Epifluorescence Microscopy"; Biophysical Journal; vol. 82; (Feb. 2002); pp. 1076-1085.
Miyawaki et al.; "Monitoring Protein Conformations and Interactions by Fluorescence Resonance Energy Transfer Between Mutants of Green Fluorescent Protein"; Methods in Enzymology, vol. 327; (2000); pp. 472-501.
Wouters et al.; "FRET Microscopy Demonstrates Molecular Association of Non-Specific Lipid Transfer Protein (nsL-TP) With Fatty Acid Oxidation Enzymes in Peroxisomes"; The EMBO Journal; vol. 17; No. 24; pp. 7179-7189; (1998).

(Continued)

*Primary Examiner*—Sam P Siefke
(74) *Attorney, Agent, or Firm*—Drinker Biddle & Reath LLP

(57) ABSTRACT

An analyzer for measuring an FRET (fluorescence resonance energy transfer) efficiency of a specimen containing a donor and an acceptor. The analyzer has an illuminator, an optical system, a detector and a calculator. The illuminator emits light for donor excitation and acceptor bleaching. The detector detects fluorescence from the specimen. The calculator calculates the FRET efficiency using the output of the detector. The detector independently detects the fluorescence in wavelength regions. One of the regions has a larger overlap with the fluorescence spectrum of the acceptor than with that of the donor.

13 Claims, 7 Drawing Sheets

OTHER PUBLICATIONS

Bastiaens et al.; "Imaging the Molecular State of Proteins in Cells by Fluorescence Resonance Energy Transfer (FRET) Sequential Photobleaching of Forster Donor-Acceptor Pairs"; Cell-Cell Communication; pp. 77-83; (1995).

HPK Catalog; Aqua Cosmos/Ashura (2003).

Miyawaki; "FRET Between Molecules With the Use of GFP"; Seitai no Kagaku; vol. 53, No. 1; (2002); pp. 75-81; w/ English Translation.

Sawano et al., "Multicolor Imaging of $Ca^{2+}$ and Protein Kinase C Signals Using Novel Epifluorescence Microscopy", Biophysical Journal, vol. 82, Feb. 2002, pp. 1076-1085.

Miyawaki et al., "Monitoring Protein Conformations and Interactions by Fluorescence Resonance Energy Transfer Between Mutants of Green Fluorescent Protein", Methods in Enzymology, vol. 327, pp. 472-500.

FLUORESCENCE RESONANCE ENERGY TRANSFER ANALYZER

BACKGROUND OF THE INVENTION

1. Field of the Invention

The present invention relates to analysis of fluorescence resonance energy transfer.

2. Related Background Art

Fluorescence resonance energy transfer (FRET) is a phenomenon in which excitation energy transfers from a fluorescent molecule to another molecule. The molecule that supplies energy to another molecule is called a donor, and the molecule that receives the energy is called an acceptor. When FRET occurs, the fluorescence of the donor weakens. When the acceptor is a fluorescent molecule, fluorescence is emitted from the acceptor.

When FRET in a cell is measured by microscopic observation, the following method may be used: measure the fluorescence intensities of the donor and the acceptor when the donor is excited, and calculate the ratio between the measured intensities, i.e., the acceptor's intensity/the donor's intensity (see Atsushi Miyawaki et al., "Fluorescent indicators for $Ca^{2+}$ based on green fluorescent proteins and calmodulin," *Nature*, vol. 388, pp. 882-887, 28 Aug., 1997). The fluorescence intensities of the donor and acceptor can be measured in turn by switching the bandpass filters disposed in front of the detector. Moreover, the fluorescence from the donor and the acceptor can be simultaneously detected with two detectors by separating the fluorescence from them with a dichroic mirror and then filtering the fluorescence with the bandpass filter. As the detector, a camera such as a cooled CCD camera, or a photomultiplier is used, for example.

By this method, change in the fluorescence where the fluorescence of the donor weakens and that of the acceptor intensifies, which is characteristic of the FRET, can be observed. Calculating the fluorescence intensity ratio between the donor and the acceptor clearly shows the amount of the change in the fluorescence intensities. Moreover, this method is advantageous because it can cancel variation in the fluorescence intensities due to the thickness of the cell, the distribution of the dyes and the illumination unevenness of the light source. However, this method is unfit for quantitative measurement of the fluorescence intensity ratio though it can detect the changes in the FRET. When the ratio between the amounts of the donors and the acceptors in a cell is changed, when the wavelength region where fluorescence is detected is changed, when the kind of the fluorescent reagent in use is changed, or when the spectral sensitivity characteristic of the detector is changed, the value of the fluorescence intensity ratio changes accordingly. Consequently, no quantitative comparison can be made between the measurement values obtained before and after these experimental conditions are changed.

An FRET efficiency (Et) is an example of a value that can be quantitatively compared even when the experimental condition changes. Et=1−Fd'/Fd is known as an expression for obtaining this, where Fd is the fluorescence intensity of the donor when no FRET occurs, and Fd' is the fluorescence intensity of the donor when FRET occurs. To determine Fd, light with the absorption wavelength of the acceptor is used to illuminate a specimen containing the donor and acceptor, all the acceptor molecules in measurement region are broken by photo-bleaching, and then the fluorescence intensity of the donor is measured. By Measuring Fd' at time intervals before this bleaching experiment, variations of Et over time can be calculated.

When the bleaching experiment is performed after the measurement of Fd', the wavelength of the illumination light and the dichroic mirror are switched from ones for Fd' measurement to ones for bleaching. Intense light not including the absorption wavelength region of the donor and including the absorption wavelength region of the acceptor as widely as possible is used to illuminate the specimen. This is done in order to bleach the acceptor as quickly as possible without the fluorescence of the donor being affected by bleaching or the like. However, the wavelength region of the light for bleaching frequently overlaps with the fluorescence wavelength region of the acceptor. Accordingly, part of the light for bleaching leaks from the dichroic mirror and enters the detector for monitoring the fluorescence of the acceptor. Since the leakage light has a very high intensity, it may be impossible to monitor the bleaching process of the acceptor by the detector.

For example, a case is assumed where the fluorescent dye ECFP is used as the donor, the fluorescent dye EYFP is used as the acceptor and the fluorescence of the donor and acceptor are measured after the separation with a filter. FIG. 7 shows the absorption spectrum 51 and the fluorescence spectrum 52 of ECFP and the absorption spectrum 53 and the fluorescence spectrum 54 of EYFP. Considering these spectra, the following bandpass filters are used: the filter having a transmission wavelength region "a" for exciting ECFP at 440 nm with the half width of 20 nm, the filter having a transmission wavelength region "c" for filtering the fluorescence of ECFP at 480 nm with the half width of 30 nm, and the filter having a transmission wavelength region "d" for filtering the fluorescence of EYFP at 535 nm with the half width of 25 nm. In this case, a dichroic mirror that allows light with wavelengths not less than 455 nm to pass therethrough is used. Thereafter, in bleaching EYFP, a bandpass filter that has a transmission wavelength region "b" at 525 nm with the half width of 45 nm is used. The filter is selected so as not to include the absorption wavelength region of ECFP and widely cover the absorption wavelength region of EYFP. In this case, a dichroic mirror of 560 nm is used (see Atsushi Miyawaki, "GFP wo mochiita bunshikan FRET (Intermolecular FRET Using GFP)," *Seitai no Kagaku*, Vol. 53, No. 1, pp. 75-81, Feb., 2002, and Asako Sawano et al., "Multicolor Imaging of $Ca^{2+}$ and Protein Kinase C Signals Using Novel Epifluorescence Microscopy," *Biophysical Journal*, Vol. 82, pp. 1076-1085, Feb., 2002). When an ND filter or the like is placed on the optical path, it is removed from the path in order to apply light as intense as possible to the specimen. Accordingly, part of this intense illumination light enters the detector for measuring EYFP in the EYFP bleaching experiment.

Therefore, in order to determine when the bleaching is completed and the illumination is to be stopped, the specimen is illuminated by the light for bleaching over a predetermined time, then the settings of the dichroic mirror, the filter and the like of the microscope are returned to the ones for the fluorescence measurement, and then the fluorescence of the acceptor is measured. Thereafter, the settings are returned to the ones for the bleaching, and the light for bleaching is used to illuminate the specimen. This operation is repeated until the fluorescence of the acceptor no longer attenuates (see Atsushi Miyawaki and Roger Y. Tsien, "Monitoring Protein Conformations and Interactions by Fluorescence Resonance Energy Transfer between Mutants of Green Fluorescent Protein," *Methods in Enzymology*, vol. 327, pp. 472-500, 2000).

Furthermore, there is a method for measuring the bleaching speed of the fluorescence of the donor to quantitatively measure the FRET efficiency. In this method, the FRET efficiency Et is expressed as $Et=1-\tau_{b1}/\tau'_{b1}$, where $\tau_{b1}$ is the bleaching speed of the donor fluorescence when no FRET occurs, and $\tau'_{b1}$ is the bleaching speed of the donor fluorescence when FRET occurs. The bleaching speed of the donor fluorescence can be obtained as the attenuation speed of the fluorescence intensity when the fluorescence intensity is measured a number of times at time intervals while the specimen is continuously illuminated by the light with the absorption wavelength of the donor. However, since the fluorescence of the donor is bleached in the measurement, variations over time of the FRET efficiency for the same specimen cannot be determined. In addition, it is necessary to set a region for determining $\tau_{b1}$ in the specimen and previously break the acceptor molecules in the region by photo bleaching (see Fred S. Wouters et al., "FRET microscopy demonstrates molecular association of non-specific lipid transfer protein (nsL-TP) with fatty acid oxidation enzymes in peroxisomes," *The EMBO Journal*, Vol. 17, No. 24, pp. 7179-7189, 1998, and Philippe I. H. Bastiaens et al., "Imaging the molecular state of proteins in cells by fluorescence resonance energy transfer (FRET) Sequential photobleaching of Forster donor-acceptor pairs," Proceedings of the Second Hamamatsu International Symposium on Biomolecular Mechanisms and Photonics: *Cell-Cell Communication*, pp. 77-82, 1995).

SUMMARY OF THE INVENTION

It is an object of the present invention to quantitatively measure an efficiency of a fluorescence resonance energy transfer with simple operation.

In one aspect, this invention relates to an FRET (fluorescence resonance energy transfer) analyzer for measuring an FRET efficiency of a specimen containing a donor and an acceptor. The analyzer comprises an illuminator for selectively emitting light for donor excitation and light for acceptor bleaching, a detector for detecting fluorescence emitted from the specimen in response to illuminating the specimen with the light for donor excitation, and generating an output corresponding to an intensity of the fluorescence, and a calculator for calculating the FRET efficiency using the output of the detector. The detector independently detects light in first, second and third wavelength regions different from one another. The first wavelength region has a larger overlap with a fluorescence spectrum of the donor than with a fluorescence spectrum of the acceptor. The second wavelength region has a larger overlap with the fluorescence spectrum of the acceptor than with the fluorescence spectrum of the donor. The third wavelength region has a larger overlap with the fluorescence spectrum of the acceptor than with the fluorescence spectrum of the donor, and has no substantial overlap with a wavelength region of the light for acceptor bleaching.

The illuminator may have an optical attenuator adapted to place a light dimming filter on an optical path. When the illuminator emits the light for donor excitation, the optical attenuator places the light dimming filter on the optical path so that the light for donor excitation passes through the light dimming filter. When the illuminator emits the light for acceptor bleaching, the optical attenuator removes the light dimming filter from the optical path so that the light for acceptor bleaching does not pass through the light dimming filter.

The illuminator may have a light source, an optical attenuator, and a wavelength selector. The light source emits light in both a wavelength region of the light for donor excitation and a wavelength region of the light for acceptor bleaching. The optical attenuator receives the light from the light source, and is adapted to place a light dimming filter on an optical path. The wavelength selector receives the light from the optical attenuator to extract either component in the wavelength region of the light for donor excitation or the optical component in the wavelength region of the light for acceptor excitation. When the illuminator emits the light for donor excitation, the optical attenuator places the light dimming filter on the optical path so that the light from the light source passes through the light dimming filter before entering the wavelength selector. When the illuminator emits the light for acceptor bleaching, the optical attenuator removes the light dimming filter from the optical path so that the light from the light source does not pass through the light dimming filter.

The third wavelength region may have an overlap with the fluorescence spectrum of the acceptor so that fluorescence emitted from the acceptor when the specimen is illuminated by the light for acceptor bleaching is detected without saturation of the detector. The third wavelength may overlap with only a low-intensity region of the fluorescence spectrum of the acceptor.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
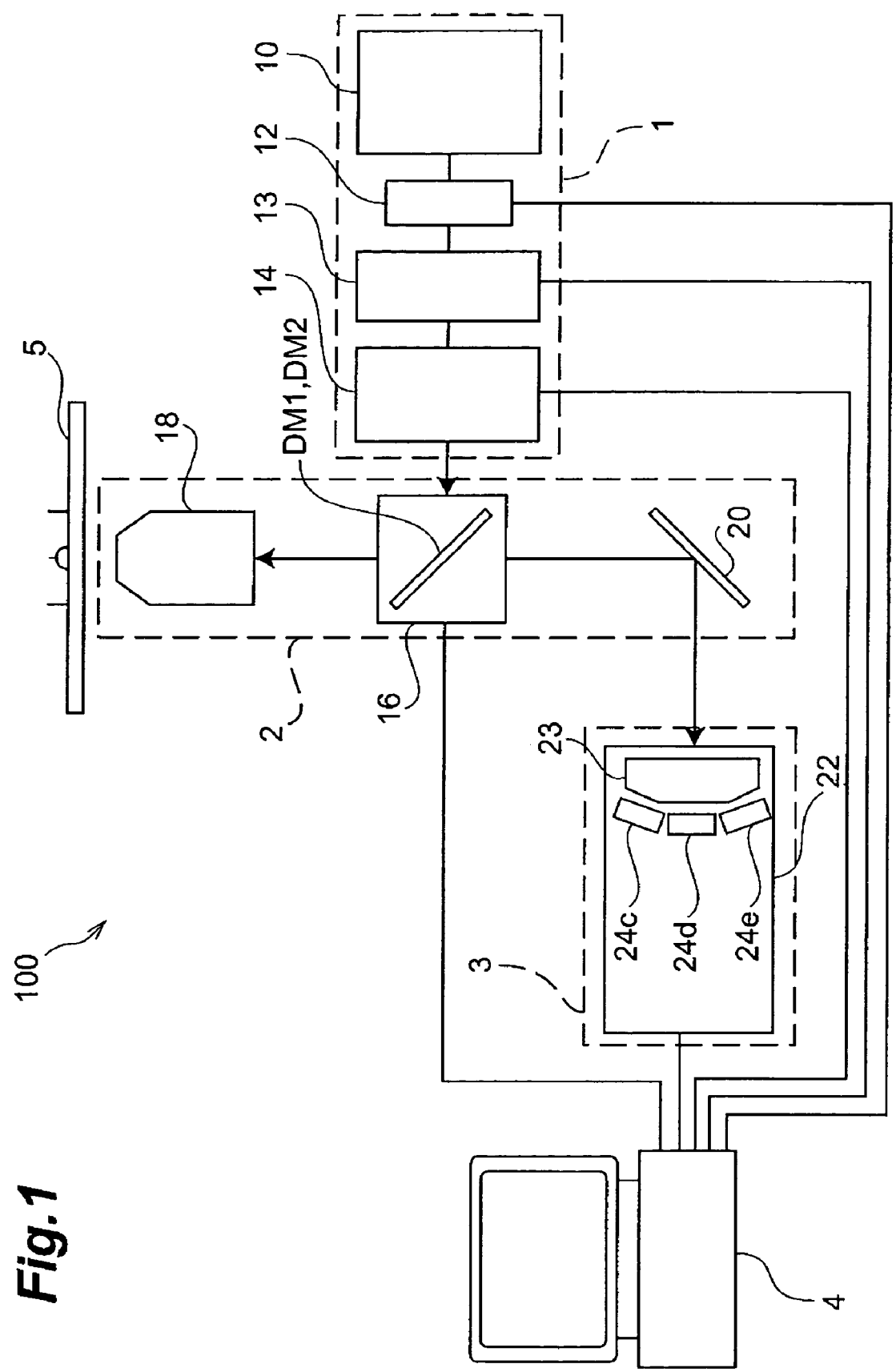
FIG. 1 is a block diagram showing the structure of an FRET analyzer of an embodiment of this invention.

The preferred embodiments of the present invention will be described below in greater detail with reference to the accompanying drawings. To facilitate understanding, identical reference numerals are used, where possible, to designate identical or equivalent elements that are common to the embodiments, and, in subsequent embodiments, these elements will not be further explained.

First Embodiment

Figure 2:
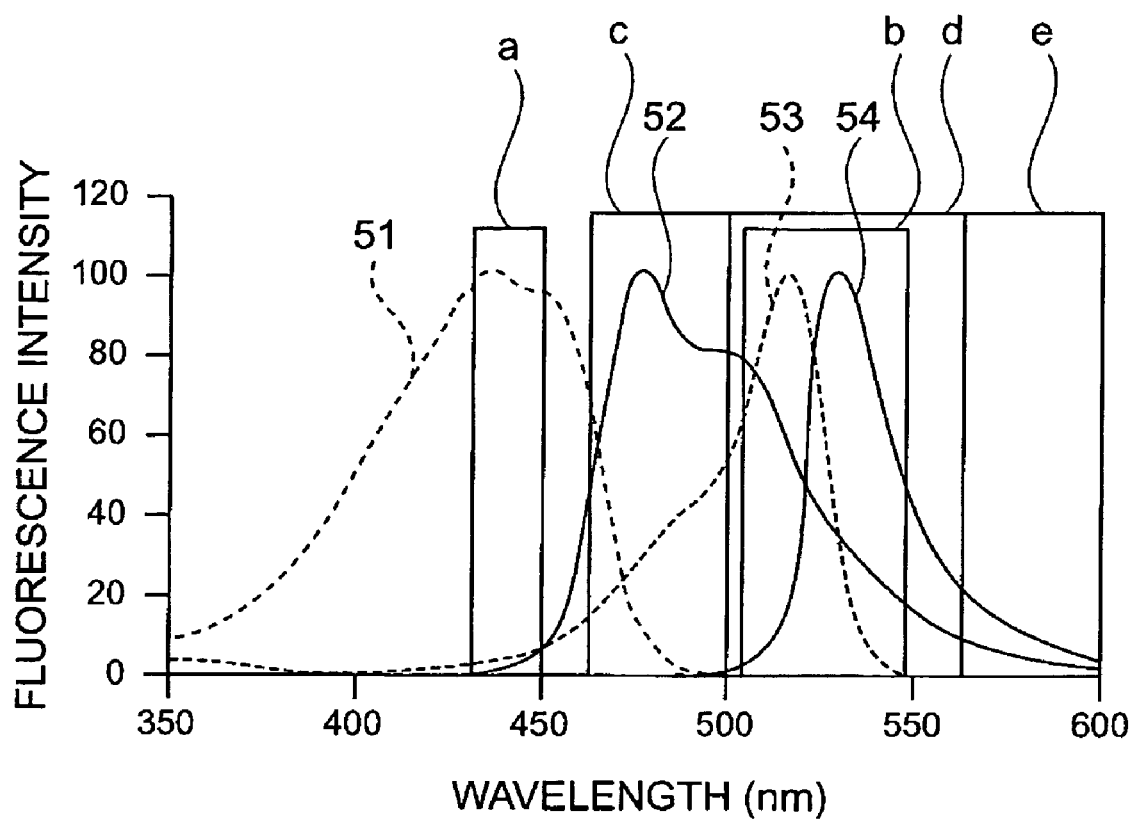
FIG. 2 is a graph showing fluorescence and absorption spectra of each of the donor and acceptor, and also showing the wavelength regions used by the FRET analyzer.

FIG. 1 is a block diagram showing the structure of an FRET (fluorescence resonance energy transfer) analyzer of this embodiment. The FRET analyzer 100 measures an FRET efficiency of a specimen 5. The specimen 5 contains fluorescent dyes ECFP and EYFP. ECFP is a donor, and EYFP is an acceptor. FIG. 2 shows the fluorescence spectrum and the absorption spectrum of each of ECFP and EYFP. FIG. 2 also shows various wavelength regions used by the FRET analyzer 100.

The FRET analyzer 100 calculates the FRET efficiency by the following expression:

$$Et = 1 - Fd'/Fd \qquad (1),$$

where Et is the FRET efficiency, Fd is the fluorescence intensity of the donor when no FRET occurs, and Fd' is the fluorescence intensity of the donor when FRET occurs.

First, the analyzer 100 causes the FRET by illuminating the specimen 5 with light for donor excitation, and measures the fluorescence intensity of the donor as Fd'. Then, the analyzer 100 breaks the acceptor by illuminating the specimen 5 with light for acceptor bleaching and measures the fluorescence intensity of the donor as Fd. The analyzer 100 calculates Et using the obtained Fd and Fd'.

As shown in FIG. 1, the FRET analyzer 100 comprises an illuminator section 1, an optical system 2, a detector section 3 and a processing section 4. The illuminator section 1, the optical system 2 and the detector section 3 are optically coupled with each other. The illuminator section 1, the optical system 2 and the detector section 3 are electrically connected to the processing section 4.

The illuminator section 1 selectively emits light for donor excitation and light for acceptor bleaching, which are to be used to illuminate the specimen 5. The illuminator section 1 has a light source 10, a shutter 12, an ND filter switcher 13, and a wavelength switcher 14 that are optically coupled with each other. The shutter 12, the ND filter switcher 13 and the wavelength switcher 14 are electrically connected to the processing section 4 through signal lines.

The light source 10 emits light in both a wavelength region for donor excitation and a wavelength region for acceptor bleaching. In the present embodiment, a white light source such as a xenon lamp is used as the light source 10.

The shutter 12 is disposed on the optical path between the light source 10 and the ND filter switcher 13. The shutter 12 controls the incidence, on the ND filter switcher 13, of the light emitted from the light source 10. The light emitted from the light source 10 enters the ND filter switcher 13 when the shutter 12 is opened, and does not enter the ND filter switcher 13 when the shutter 12 is closed.

The ND filter switcher 13 is an optical attenuator for reducing the intensity of the light emitted from the light source 10. The ND filter switcher 13 receives the light from the shutter 12 and transmits it to the wavelength switcher 14. The ND filter switcher 13 includes a plurality of ND filters as light dimming filters. These ND filters have transmittances different from one another (for example, 10%, 1%, and 0.1%).

When causing FRET, the ND filter switcher 13 places one of the ND filters on the optical path. The light for donor excitation passes through the placed ND filter and its intensity is reduced. By placing an appropriate ND filter on the optical path, a fluorescent image of the specimen 5 having intensity appropriate to the sensitivity of the detector section 3 can be transmitted to the detector section 3.

Moreover, it is possible for the ND filter switcher 13 to place none of the ND filters on the optical path. In this case, the light transmittance of the ND filter switcher 13 is substantially 100%. As mentioned later, when the acceptor is bleached, the ND filter switcher 13 removes the ND filter from the optical path. Accordingly, the light for acceptor bleaching does not pass through the ND filter, so that its intensity is not lowered.

The light emitted from the light source 10 passes through the shutter 12 and the ND filter switcher 13, and then enters the wavelength switcher 14. The wavelength switcher 14 switchably extracts a specific wavelength component from the light emitted from the light source 10. That is, the wavelength switcher 14 is a kind of filter device. The wavelength switcher 14 can be formed by use of a monochromater, a bandpass filter, or other wavelength selecting means.

When receiving the light from the light source 10, the wavelength switcher 14 transmits a component of the light having either a wavelength region $\lambda_{ex1}$ or a wavelength region $\lambda_{ex2}$. $\lambda_{ex1}$ is the wavelength region not less than 430 nm and not more than 450 nm with the center wavelength of 440 nm and the half width of 20 nm. $\lambda_{ex2}$ is the wavelength region not less than 502.5 nm and not more than 547.5 nm with the center wavelength of 525 nm and the half width of 45 nm. Light in the wavelength region $\lambda_{ex1}$ excites the donor ECFP in the specimen 5 so as to cause fluorescence. Light in the wavelength region $\lambda_{ex2}$ bleaches the acceptor EYFP in the specimen 5. The wavelength regions $\lambda_{ex1}$ and $\lambda_{ex2}$ are determined in consideration of the absorption spectra of both the donor ECFP and the acceptor EYFP.

The absorption spectra of ECFP and EYFP are shown in FIG. 2. In FIG. 2, the broken line 51 shows the absorption spectrum of ECFP, and the broken line 53 shows the absorption spectrum of EYFP. The solid line "a" shows the wavelength region $\lambda_{ex1}$, and the solid line "b" shows the wavelength region $\lambda_{ex2}$. The wavelength region $\lambda_{ex1}$ overlaps with the absorption spectrum 51 of ECFP, and includes the peak wavelength of the absorption spectrum 51. The wavelength region $\lambda_{ex2}$ overlaps with the absorption spectrum 53 of EYFP, and includes the peak wavelength of the absorption spectrum 53. The wavelength region $\lambda_{ex2}$ does not overlap with the absorption spectrum 51 of ECFP.

The optical system 2 receives the light emitted from the illuminator section 1, and sends it to the specimen 5. Moreover, the optical system 2 receives fluorescence emitted from the specimen 5 and sends it to the detector section 3. The optical system 2 prevents the light reflected at the specimen 5 from the illuminator section 1 from entering the detector section 3. Regarding the FRET analyzer 100 as a microscope, the optical system 2 corresponds to an epi-illumination optical system.

The optical system 2 has a dichroic mirror switcher 16, an objective lens system 18 and a total reflection mirror 20 that are optically coupled with each other. The dichroic mirror switcher 16 is also optically coupled with the wavelength switcher 14 of the illuminator section 1. Moreover, the dichroic mirror switcher 16 is electrically connected to the processing section 4 through a signal line.

The light exiting from the wavelength switcher 14 enters the dichroic mirror switcher 16. The dichroic mirror switcher 16 includes two dichroic mirrors DM1 and DM2 having different characteristics. The dichroic mirror switcher 16 selectively places one of these dichroic mirrors on the optical path. Accordingly, the light from the wavelength switcher 14 enters one of the dichroic mirrors. Which mirror is placed on the optical path is determined on an instruction from the processing section 4. The dichroic mirror DM1 transmits light with the wavelengths not less than 455 nm, and reflects light with the wavelengths less than 455 nm. The dichroic mirror DM2 transmits light with the wavelengths not less than 560 nm, and reflects light with the wavelengths less than 560 nm. These dichroic mirrors are used for reflecting the light from the illuminator section 1 toward the specimen 5, and for blocking the reflected light to prevent its incidence on the detector section 3.

The objective lens system 18 is disposed between the dichroic mirror switcher 16 and the specimen 5. In other words, when the FRET analysis of the specimen 5 is performed, the specimen 5 is disposed so as to face the objective lens system 18. The objective lens system 18 receives the light exiting from the illuminator section 1 to be reflected at the dichroic mirror DM1 or DM2, and condenses and applies the received light to the specimen 5. Moreover, the objective lens system 18 receives the fluorescence emitted from the specimen 5, and transmits it to the dichroic mirror switcher 16.

The total reflection mirror 20 is disposed on the opposite side of the dichroic mirror switcher 16 from the objective lens system 18. The total reflection mirror 20 receives the fluorescence emitted from the specimen 5 through the objective lens system 18 and the dichroic mirror switcher 16. The total reflection mirror 20 reflects the received fluorescence at a high reflectance toward the detector section 3.

The detector section 3 is composed of a triple CCD camera 22. The triple CCD camera 22 is an imaging device that detects fluorescence emitted from the specimen 5 and takes images of the detected fluorescence. The triple CCD camera 22 receives the fluorescence emitted from the specimen 5 and reflected at the total reflection mirror 20, and generates output electric signals corresponding to the intensities of the fluorescence. The output signal is representative of a spatial distribution image of the fluorescence (hereinafter, referred to as "fluorescent image") on the specimen 5. The output signals are sent to the processing section 4.

The triple CCD camera 22 has a prism 23 and three CCD chips 24c to 24e. The prism 23 is disposed on the light incident portion of the CCD camera 22. The light from the total reflection mirror 20 enters the incident surface of the prism 23. The CCD chips 24c to 24e face the exit surface of the prism 23. The prism 23 is a spectroscope. When receiving the light from the total reflection mirror 20, the prism 23 disperses the light in the directions corresponding to the wavelengths of the light. The spectral characteristic of the prism 23 is determined so that lights in different wavelength regions $\lambda_{em1}$ to $\lambda_{em3}$ enter the CCD chips 24c to 24e, respectively. These wavelength regions do not substantially overlap with one another. Each of the CCD chips 24c to 24e is the photodetector that generates an output electric signal corresponding to the intensity of the incident light. Accordingly, the CCD camera 22 is capable of independently detecting the components, in the different wavelength regions $\lambda_{em1}$ to $\lambda_{em3}$, of the incident light. In the present embodiment, $\lambda_{em1}$ is a wavelength region not less than 460 nm and less than 500 nm, $\lambda_{em2}$ is a wavelength region not less than 500 nm and less than 565 nm, and $\lambda_{em3}$ is a wavelength region not less than 565 nm and not more than 600 nm. The wavelength regions $\lambda_{em1}$ to $\lambda_{em3}$ are determined in consideration of the fluorescence spectra of both the donor ECFP and the acceptor EYFP.

The fluorescence spectrum of each of ECFP and EYFP is shown in FIG. 2. In FIG. 2, the solid line 52 shows the fluorescence spectrum of ECFP, and the solid line 54 shows the fluorescence spectrum of EYFP. The solid line "c" shows the wavelength region $\lambda_{em1}$, the solid line "d" shows the wavelength region $\lambda_{em2}$, and the solid line "e" shows the wavelength region $\lambda_{em3}$. The wavelength region $\lambda_{em1}$ overlaps with the fluorescence spectrum 52 of ECFP, and includes the peak wavelength of the fluorescence spectrum 52. The wavelength region $\lambda_{em1}$ hardly overlaps with the fluorescence spectrum 54 of EYFP. The wavelength region $\lambda_{em2}$ overlaps with the fluorescence spectrum 54 of EYFP, and includes the peak wavelength of the fluorescence spectrum 54. The wavelength region $\lambda_{em2}$ also overlaps with the fluorescence spectrum 52 of ECFP. The wavelength region $\lambda_{em3}$ overlaps with both the fluorescence spectra 52 and 54.

As shown in FIG. 2, the overlap between the wavelength region $\lambda_{em1}$ and the fluorescence spectrum 54 of EYFP is extremely small. Consequently, the output of the CCD chip 24c receiving the fluorescent component in the wavelength region $\lambda_{em1}$ is substantially representative of the intensity of the fluorescence of ECFP. Thus the wavelength region $\lambda_{em1}$ is determined so that the output of the detector 4 associated with the wavelength region $\lambda_{em1}$ is representative of the fluorescence intensity of ECFP. Generally, when the overlap between the wavelength region $\lambda_{em1}$ and the fluorescence spectrum 52 of ECFP is sufficiently larger than the overlap between the wavelength region $\lambda_{em1}$ and the fluorescence spectrum 54 of EYFP, the output of the wavelength region $\lambda_{em1}$, (the output of the CCD chip 24c) can be treated as being representative of the fluorescence intensity of ECFP. In this specification, the "overlap between the wavelength region and the spectrum" means the integral of the spectrum intensity over the wavelength region.

The wavelength region $\lambda_{em2}$ has a larger overlap with the fluorescence spectrum 54 of EYFP than with the fluorescence spectrum 52 of ECFP. The overlap between the wavelength region $\lambda_{em2}$ and the fluorescence spectrum 54 of EYFP is sufficiently larger than the overlap between the wavelength region $\lambda_{em2}$ and the fluorescence spectrum 52 of ECFP. Consequently, the output of the detector 4 associated with the wavelength region $\lambda_{em2}$ (the output of the CCD chip 24d) can be treated as being representative of the fluorescence intensity of EYFP. Thus the wavelength region $\lambda_{em2}$ is determined so that the output of the detector 4 associated with the wavelength region $\lambda_{em2}$ is representative of the fluorescence intensity of EYFP.

The wavelength region $\lambda_{em3}$ also has a larger overlap with the fluorescence spectrum 54 of EYFP than with the fluorescence spectrum 52 of ECFP. Moreover, the wavelength region $\lambda_{em3}$ does not overlap with the wavelength region $\lambda_{ex2}$ of the light for acceptor bleaching. The overlap between the wavelength region $\lambda_{em3}$ and the fluorescence spectrum 54 of EYFP is sufficiently larger than the overlap between the wavelength region $\lambda_{em3}$ and the fluorescence spectrum 52 of ECFP. The wavelength region $\lambda_{em3}$ is used for measuring the fluorescence intensity of EYFP during bleaching the EYFP. As mentioned later, when EYFP is bleached, light in the wavelength region $\lambda_{ex2}$ not including the absorption wavelength of ECFP and widely including the absorption wavelength of EYFP is used to illuminate the specimen 5. Accordingly, most of the fluorescence detected in the wavelength region $\lambda_{em3}$ is the fluorescence emitted from EYFP. Therefore, the output of the detector 4 associated with the wavelength region $\lambda_{em3}$ (the output of the CCD chip 24e) can be treated as being representative of the fluorescence intensity of EYFP during its bleaching.

The processing section 4 is a computer system. The processing section 4 acts both as a controller for controlling the measurement of the FRET efficiency and as a calculator for calculating the FRET efficiency using the output of the detector section 3. The processing section 4 controls operations of the shutter 12, the ND filter switcher 13, the wavelength switcher 14, the dichroic mirror switcher 16 and the CCD camera 22 to perform the donor excitation and acceptor bleaching of the specimen 5. Moreover, the processing section 4 performs the FRET analysis process by use of the output signal of the CCD camera 22. The processing section 4 includes a display unit. The processing section 4 displays the result of the FRET analysis on the screen of the display unit.

Figure 3:
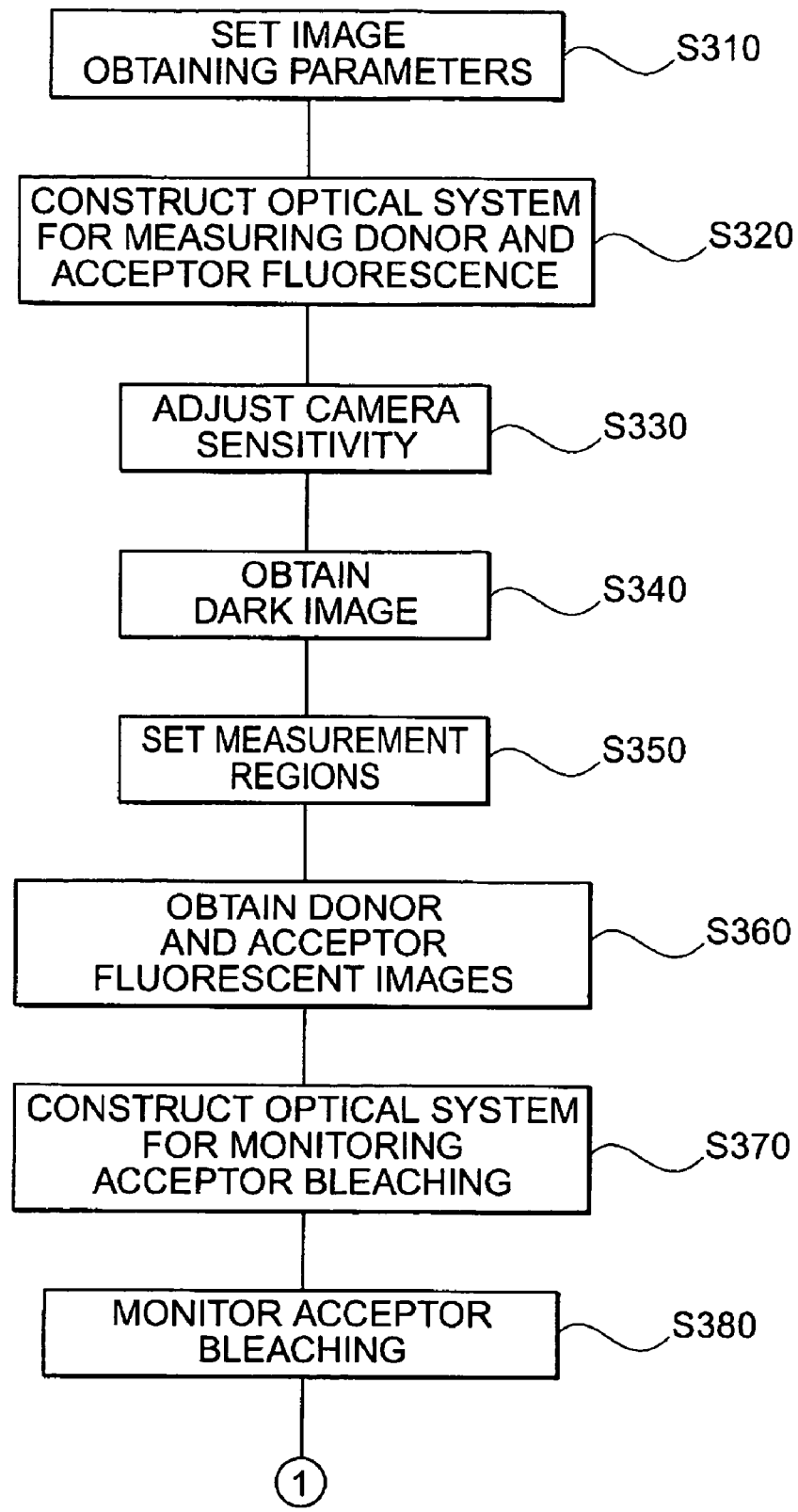
FIGS. 3 and 4 are flowcharts showing FRET analysis procedures.
Figure 4:
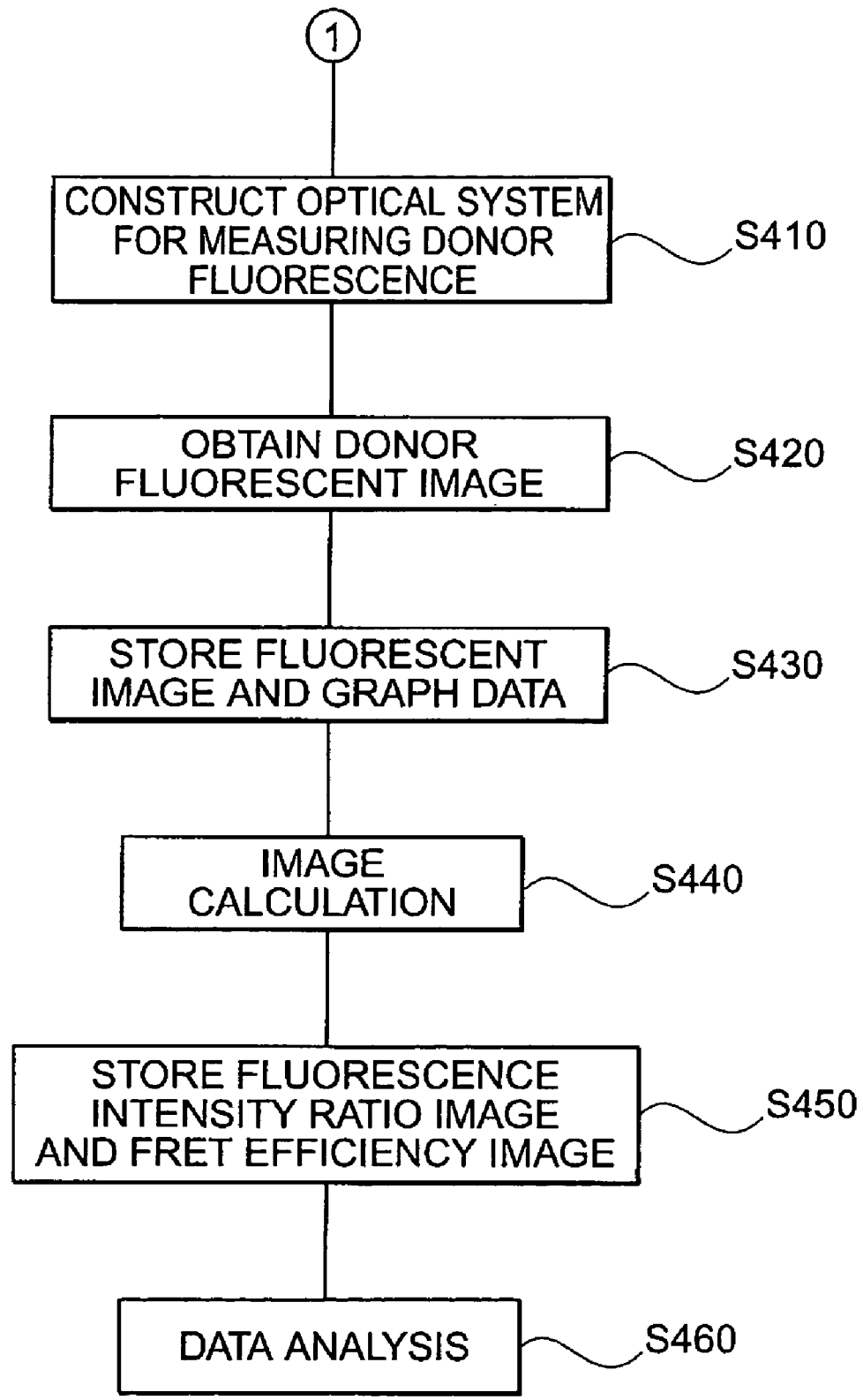

The procedures of the FRET analysis using the analyzer 100 will now be described with reference to FIGS. 3 and 4, which are flowcharts showing the analysis procedures.

When starting the FRET analysis, the operator sets the image obtaining parameters by operating the processing section 4 (step S310). This includes the setting for measuring the donor and acceptor fluorescence and the setting for monitoring the acceptor bleaching. The number of images to be obtained by the CCD camera 22, the time interval of the image obtaining and the like are set as parameters for the fluorescence measurement. The time interval of the fluorescence intensity measurement by the CCD camera 22, the intensity or attenuation rate of the fluorescence at which the monitoring of the acceptor bleaching is to stop and the like are set as parameters for the monitoring of the bleaching.

Then, the analyzer 100 constructs an optical system for measuring the fluorescence from the donor and acceptor (step S320). At this step, the processing section 4 sends a control signal to the wavelength switcher 14 so that the transmission wavelength region of the wavelength switcher 14 is set to $\lambda_{ex1}$. Moreover, the processing section 4 sends a control signal to the ND filter switcher 13 so as to select one of the ND filters and sets the selected filter on the optical path. Further, the processing section 4 sends a control signal to the dichroic mirror switcher 16 so as to set the dichroic mirror DM1 on the optical path.

The sensitivity of the CCD camera 22 is adjusted (step S330). The operator sets the exposure time and gain of the CCD camera 22 by operating the processing section 4.

Then, a dark image is obtained using the CCD camera 22 (step S340). The data of the dark image is sent from the CCD camera 22 to the processing section 4. The dark image data is used for correcting the data of the fluorescent images of the specimen 5.

The operator sets measurement regions (imaging regions) on the specimen 5 by operating the processing section 4 (step S350). This includes the setting of the region where the intensities of the fluorescence of the donor and acceptor are measured and the setting of the region where the bleaching of the acceptor is monitored.

When the above-described preparations are completed, the analyzer 100 obtains the fluorescent image of each of the donor and the acceptor under the set condition (step S360). This step will be described in detail hereinafter.

The processing section 4 repeatedly opens and closes the shutter 12 at the time intervals set at step S310. When the shutter 12 is opened, the white light emitted from the light source 10 passes through the ND filter in the ND filter switcher 13 to enter the wavelength switcher 14. The intensity of the light is decreased by the ND filter. The wavelength switcher 14 transmits only the component in the wavelength region $\lambda_{ex1}$, and blocks the other wavelength components. The light for donor excitation is generated in this way. The light for donor excitation exits from the wavelength switcher 14 to be reflected at the dichroic mirror DM1, passes through the objective lens system 18, and is then applied to the specimen 5. Consequently, the donor, or ECFP, in the specimen 5 is excited to cause fluorescence.

The fluorescence emitted from the specimen 5 includes the one emitted from EYFP (the acceptor) having received excitation energy from ECFP through the FRET as well as the one emitted from ECFP itself. As shown by reference numerals 52 and 54 in FIG. 2, the fluorescence of ECFP and the fluorescence of EYFP have different wavelength regions. The fluorescence of ECFP and EYFP passes through the objective lens system 18 to enter the dichroic mirror switcher 16.

As mentioned above, the dichroic mirror DM1 transmits light with wavelengths not less than 455 nm, and reflects light with wavelengths less than 455 nm. Therefore, most of the fluorescence emitted from ECFP and EYFP passes through the dichroic mirror DM1. This fluorescence is reflected by the total reflection mirror 20 to enter the CCD camera 22.

On the other hand, the donor excitation light reflected at the specimen 5 is blocked by the dichroic mirror DM1. This is because the donor excitation light has the wavelength region $\lambda_{ex1}$, of 430 to 450 nm. The donor excitation light is prevented from entering the CCD camera 22 in this way.

The prism 23 in the CCD camera 22 disperses the incident fluorescence and sends it to the CCD chips 24c, 24d or 24e in accordance with the wavelength regions of the incident fluorescence. This enables the fluorescent images of ECFP and EYFP to be obtained. As mentioned above, the fluorescence of ECFP is mainly detected by the CCD chip 24c, and the fluorescence of EYFP is mainly detected by the CCD chip 24d.

The processing section 4 subtracts the dark component of the CCD chip 24c from the output of the CCD chip 24c, and converts the obtained value into the fluorescence intensity of ECFP. Moreover, the processing section 4 subtracts the dark component of the CCD chip 24d from the output of the CCD chip 24d, and converts the obtained value into the fluorescence intensity of EYFP. This calculation is performed pixel by pixel. The fluorescent images of ECFP and EYFP are determined in this way. The processing section 4 calculates the fluorescence intensity ratio expressed by (the fluorescence intensity of EYFP)/(the fluorescence intensity of ECFP). The processing section 4 displays the calculated value of the fluorescence intensity ratio on the display unit.

The processing section 4 repeats the above-described fluorescent image obtaining the number of times that is set at step S310. Each time the fluorescent images are obtained, the fluorescence intensity ratio is displayed. The fluorescence intensity of ECFP at each measurement time is the Fd' (see the expression (1) shown above) at that time.

When the fluorescent image obtaining is finished, the analyzer 100 constructs an optical system for monitoring the acceptor bleaching (step S370). The processing section 4 sends a control signal to the wavelength switcher 14 so as to change the transmission wavelength region thereof from $\lambda_{ex1}$ to $\lambda_{ex2}$. Moreover, the processing section 4 sends a control signal to the ND filter switcher 13 so as to remove the ND filter from the optical path. Further, the processing section 4 sends a control signal to the dichroic mirror switcher 16 so as to place the dichroic mirror DM2 on the optical path instead of the dichroic mirror DM1.

Then, the monitoring of the acceptor bleaching is started (step S380). The wavelength switcher 14 transmits only the component in the wavelength region $\lambda_{ex2}$ and blocks the other wavelength components. The light for acceptor bleaching is generated in this way. The bleaching light exits from the wavelength switcher 14 to be reflected at the dichroic mirror DM2, passes through the objective lens system 18, and is then applied to the specimen 5. Consequently, the acceptor, or EYFP, in the specimen 5 starts bleaching. The bleaching light for illuminating the specimen 5 has a high intensity because it is not attenuated by the ND filter. Therefore, the light is capable of efficiently bleaching the acceptor.

As shown by the solid line "b" in FIG. 2, the wavelength region $\lambda_{ex2}$ of the bleaching light does not include the absorption wavelength of ECFP, and widely includes the absorption wavelength of EYFP. Consequently, most of the fluorescence emitted from the specimen 5 is the fluorescence generated from EYFP. This fluorescence passes through the objective lens system 18 to enter the dichroic mirror switcher 16.

As mentioned above, the dichroic mirror DM2 transmits light with wavelengths not less than 560 nm and reflects light with wavelengths less than 560 nm. Therefore, as is apparent from the fluorescence spectrum 54 of EYFP shown in FIG. 2, only part of the fluorescence of EYFP passes through the dichroic mirror DM2. This fluorescence is reflected by the total reflection mirror 20 to enter the CCD camera 22.

On the other hand, the acceptor bleaching light reflected at the specimen 5 is blocked by the dichroic mirror DM2. This is because the acceptor bleaching light has the wavelength region $\lambda_{ex2}$ of 502.5 to 547.5 nm. The acceptor bleaching light is prevented from entering the CCD camera 22 in this way.

Most of the fluorescence incident on the CCD camera 22 is detected by the CCD chip 24e having the wavelength region $\lambda_{em3}$ not less than 565 nm and not more than 600 nm. This is because the dichroic mirror DM2 transmits fluorescence of wavelengths not less than 560 nm. Since the wavelength region $\lambda_{ex2}$ of the bleaching light does not overlap with the absorption spectrum of ECFP as mentioned above, ECFP hardly emits fluorescence during the bleaching. Moreover, since the detection wavelength region $\lambda_{em3}$ does not overlap with the wavelength region $\lambda_{ex2}$ of the bleaching light, even if the bleaching light leaks from the dichroic mirror DM2 to enter the detector section 3, the leakage light is not detected in the wavelength region $\lambda_{em3}$. Therefore, the output of the CCD chip 24e is representative of the fluorescence intensity of EYFP during its bleaching.

The bleaching light which is not attenuated by the ND filter has a high intensity, and the intensity of the fluorescence of EYFP is high accordingly. If fluorescence having an excessive intensity enters the CCD chip 24e, the CCD chip 24e is saturated, so that the fluorescence intensity cannot be measured. However, the detection wavelength region $\lambda_{em3}$ of the CCD chip 24e overlaps with only the foot of the fluorescence spectrum 54 of EYFP at its longer wavelength side. The fluorescence intensity is low at the foot of the fluorescence spectrum 54. Therefore, the CCD chip 24e is capable of detecting EYFP fluorescence with an appropriate intensity that does not saturate the CCD chip 24e. Thus the CCD chip 24e is capable of appropriately detecting the fluorescence of EYFP and obtaining the fluorescent images while the specimen 5 is illuminated by the bleaching light.

The processing section 4 subtracts the dark component of the CCD chip 24e from the output of the CCD chip 24e, and converts the obtained value into the fluorescence intensity of EYFP. This calculation is performed pixel by pixel. The fluorescent image of EYFP during the bleaching is obtained in this way. The processing section 4 displays the obtained value of the fluorescence intensity on the display unit.

The processing section 4 repeats the above-described obtaining of the EYFP fluorescent image during bleaching at the time intervals that is set at step S310. Each time the EYFP fluorescent image is obtained, the fluorescence intensity is displayed. The processing section 4 also calculates the attenuation rate of the fluorescence intensity each time the image is obtained. The attenuation rate A is calculated by the following expression:

$$A = 1 - I_t/I_{t-1} \quad (2),$$

where $I_t$ is the fluorescence intensity of the acceptor at the time of the current image obtaining, and $I_{t-1}$ is the fluorescence intensity of the acceptor obtained at the time of the previous image obtaining. The attenuation rate A approaches zero as the bleaching of the acceptor advances.

Each time the fluorescent image is obtained, the processing section 4 compares the calculated fluorescence intensity or attenuation rate with the value that is set at step S310. When the fluorescence intensity or the attenuation rate is lower than the value set at step S310, the processing section 4 determines that the bleaching of EYFP is completed, and stops the monitoring of the bleaching. Thus the processing section 4 determines whether the bleaching of the acceptor is completed or not according to the fluorescence intensity of the acceptor during its bleaching.

When determining that the bleaching of the acceptor is completed, the processing section 4 constructs an optical system for measuring the fluorescence of ECFP, which is the donor (step S410). The processing section 4 sends a control signal to the wavelength switcher 14 so as to return the transmission wavelength region thereof from $\lambda_{ex2}$ to $\lambda_{ex1}$. Moreover, the processing section 4 sends a control signal to the ND filter switcher 13 so as to place the same ND filter as that used at step S320 on the optical path. Further, the processing section 4 sends a control signal to the dichroic mirror switcher 16 so as to again place the dichroic mirror DM1 on the optical path instead of the dichroic mirror DM2.

Then, the light in the wavelength region $\lambda_{ex1}$ is again applied from the illuminator section 1 to the specimen 5, and the fluorescent image of the donor is obtained by the CCD chip 24c in the CCD camera 22 (step S420). This is performed in a similar manner to the above-described step S360. The processing section 4 subtracts the dark component from the output of the CCD chip 24c, and converts the obtained value into the fluorescence intensity value of the donor ECFP. This value is representative of the donor fluorescence intensity Fd when no FRET occurs. This calculation is performed pixel by pixel.

Then, the processing section 4 stores the data of the obtained fluorescent images and the created graphs (step S430). These data are stored in a storage device provided in the processing section 4. The brightness of each pixel in the fluorescent image is representative of the intensity of the fluorescence emitted from the position, corresponding to the pixel, on the specimen 5.

Then, the processing section 4 performs image calculation to generate a fluorescence intensity ratio image and an FRET efficiency image at each measurement time (step S440). The fluorescence intensity ratio image is an image having the fluorescence intensity ratio, or (the fluorescence intensity of EYFP)/(the fluorescence intensity of ECFP), calculated at step S360 as the brightness for each pixel. The FRET efficiency image is an image having the FRET efficiency calculated pixel by pixel as the brightness for each pixel. As described above, the processing section 4 calculates the FRET efficiency Et according to the following expression:

$$Et = 1 - Fd'/Fd \quad (1).$$

The values calculated at steps S360 and S420 are substituted into Fd' and Fd, respectively. The calculation of the expression (1) is performed pixel by pixel. By doing this, the spatial distribution of the FRET efficiency on the specimen 5 can be represented as an image.

The processing section 4 stores the calculated data of each of the fluorescence intensity ratio image and the FRET efficiency image data (step S450). These data are stored in the storage device provided in the processing section 4.

Then, the processing section 4 starts the analysis of the fluorescence intensity ratio image and the FRET efficiency image (step S460). In this analysis, the spatial distribution and the variations with time of the FRET efficiency on the specimen 5 are analyzed. The result of the analysis may be shown using pseudo colors, graphs or numerical values on the screen of the display unit of the processing section 4.

Advantages of this embodiment will now be described. The FRET analyzer 100 is capable of continuously monitoring the bleaching process of the acceptor. That is, the analyzer 100 is capable of measuring in real time the fluorescence intensity of the acceptor during its bleaching while illuminating the specimen 5 with the light for acceptor bleaching. This is because the detector section 3 has the detection wavelength region $\lambda_{em3}$ suitable for the measurement of the fluorescence intensity of the acceptor. Hence, it is unnecessary to stop the illumination by the bleaching light and reconstruct the optical system, like in the prior art, in order to measure the fluorescence intensity of the acceptor during the bleaching. According to the analyzer 100, it is possible to find the time of completion of the acceptor bleaching based on the output in the wavelength region $\lambda_{em3}$ of the detector section 3 while continuously illuminating the specimen 5 with the bleaching light. It is possible to omit a complicated operation of switching the wavelengths of the light for illuminating the specimen and the optical systems over and over again during the bleaching in order to check the degree of advance of the bleaching. Consequently, according to the analyzer 100, the quantitative measurement of the FRET efficiency can be quickly performed by an easy operation.

Moreover, since the analyzer 100 measures the fluorescence intensity of the acceptor during its bleaching in real time, the time of illuminating the specimen 5 with the intense light for the bleaching can be minimized. Accordingly, it is possible to minimize influences on the specimen 5 such as formation abnormalities and breakage of cells of the specimen 5. For example, if the thickness of the specimen 5 changes as the formation of the cell changes, a change in the fluorescence intensity not dependent on FRET is caused. Consequently, the FRET efficiency cannot be precisely determined. In the present embodiment, this problem is prevented, and the FRET efficiency can be measured precisely.

Second Embodiment

Figure 5:
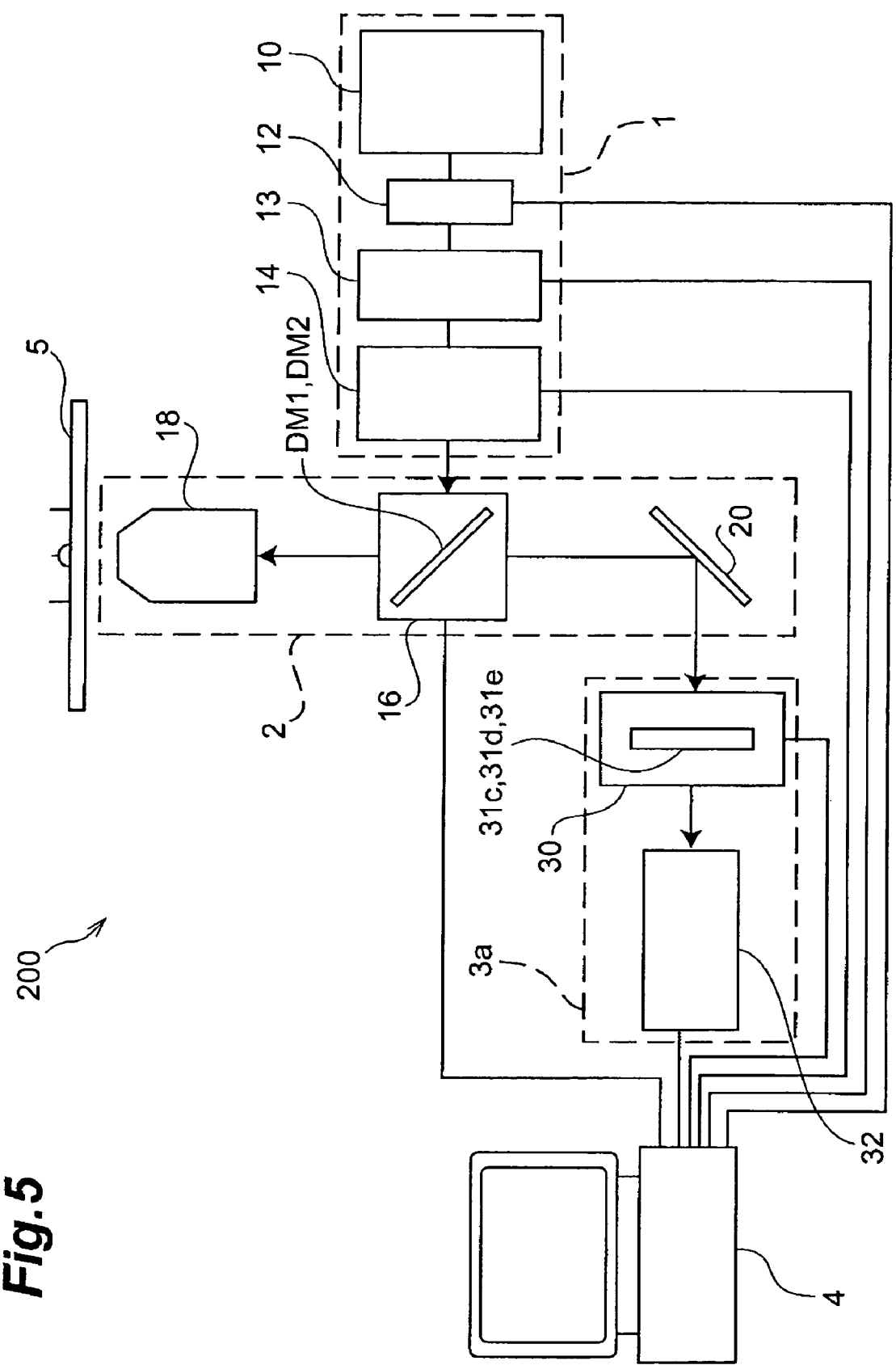
FIG. 5 is a block diagram showing structure of an FRET analyzer of another embodiment.

A second embodiment of the present invention will now be described. FIG. 5 is a block diagram showing the structure of an FRET analyzer 200 according to this embodiment. The FRET analyzer 200 has a detector section 3a instead of the detector section 3 of the analyzer 100 of the first embodiment. Except for this, the structure is the same as that of the analyzer 100.

The detector section 3a has a filter switcher 30 and a photodetector 32. The filter switcher 30 is optically coupled to the photodetector 32 and the total reflection mirror 20. The filter switcher 30 and the photodetector 32 are electrically connected to the processing section 4.

The filter switcher 30 includes three bandpass filters 31c, 31d and 31e. The filter switcher 30 selectively places one of these filters on the optical path. The fluorescence from the specimen 5 enters one of the filters. Which filter is placed on the optical path is determined on an instruction from the processing section 4. The filters 31c to 31e have the wavelength regions $\lambda_{em1}$ to $\lambda_{em3}$, respectively. Therefore, the filter switcher 30 transmits the component, in one of the wavelength regions $\lambda_{em1}$ to $\lambda_{em3}$, of the incident fluorescence.

The fluorescence, in the wavelength region $\lambda_{em1}$, $\lambda_{em2}$ or $\lambda_{em3}$, exiting from the filter switcher 30 enters the photodetector 32. The photodetector 32 is, for example, an imaging device such as a cooled CCD camera, or a photomultiplier. The photodetector 32 generates output electric signals corresponding to the intensities of the incident fluorescence. The output signals are transmitted to the processing section 4. Thus the detector section 3a independently detects the fluorescent components in the wavelength regions $\lambda_{em1}$, $\lambda_{em2}$ and $\lambda_{em3}$ by filtering the fluorescence from the specimen 5 using the filter switcher 30. Hence, in the present embodiment, the FRET efficiency can also be measured by the procedures shown in FIGS. 3 and 4. When the fluorescent images of the donor and the acceptor are obtained at step S360, switching between the filters 31c and 31d is made at high speed.

The FRET analyzer 200 has the same advantages as the analyzer 100 of the first embodiment. Since the apparatus 200 has the detection wavelength region $\lambda_{em3}$, it is capable of measuring the fluorescence intensity of the acceptor during its bleaching in real time, similarly to the analyzer 100. Accordingly, the quantitative measurement of the FRET efficiency can be quickly performed by an easy operation. Moreover, by minimizing the time of illuminating the specimen 5 with the intense light for the bleaching to reduce the influences on the specimen 5, the FRET efficiency can be measured precisely.

Third Embodiment

Figure 6:
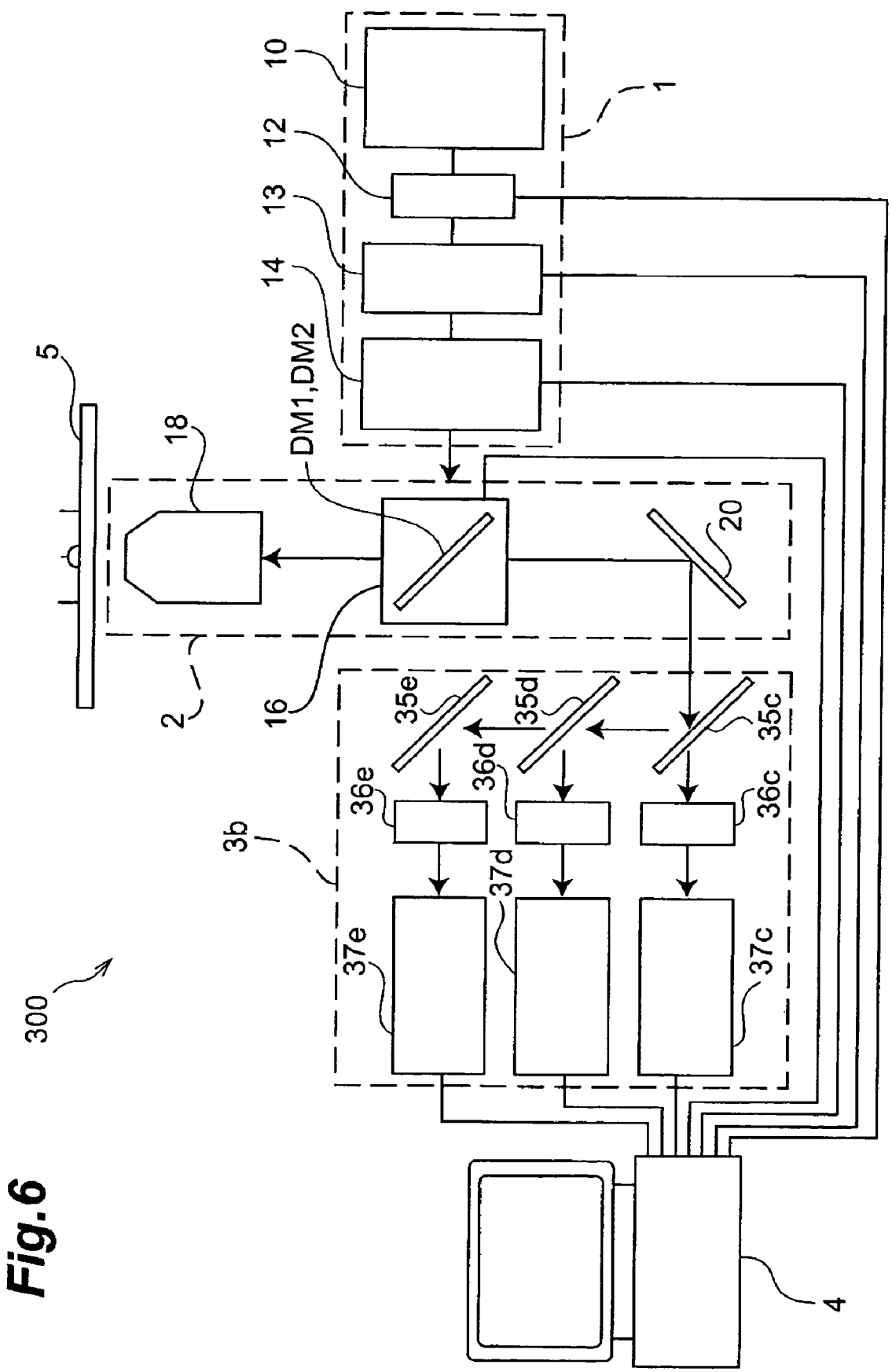
FIG. 6 is a block diagram showing structure of an FRET analyzer of still another embodiment.
Figure 7:
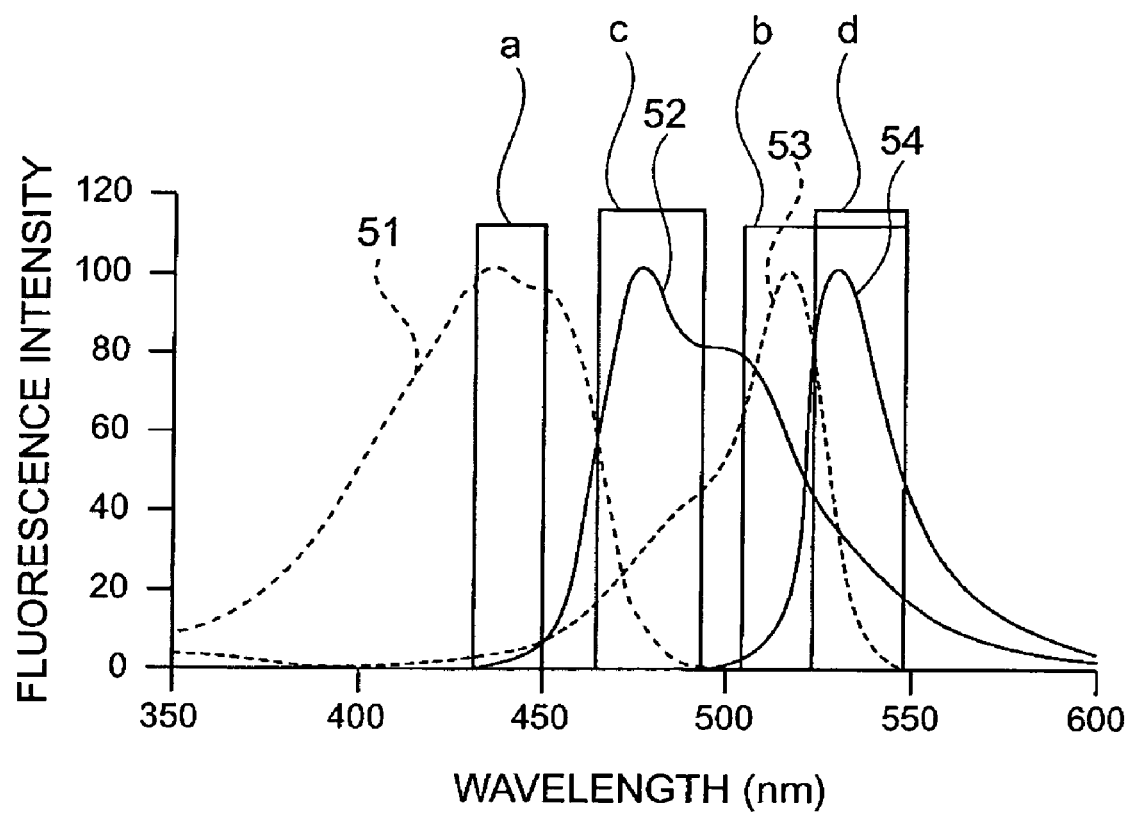
FIG. 7 is a graph showing fluorescence and absorption spectra of each of the donor and acceptor, and also showing the wavelength regions used by the FRET analyzer of the prior art.

A third embodiment of the present invention will now be described. FIG. 6 is a block diagram showing the structure of an FRET analyzer 300 according to this embodiment. The FRET analyzer 300 has a detector section 3b instead of the detector section 3 of the analyzer 100 of the first embodiment. Except for this, the structure is the same as that of the analyzer 100 of the first embodiment.

The detector section 3b has three dichroic mirrors 35c to 35e, three bandpass filters 36c to 36e and three photodetectors 37c to 37e. The dichroic mirror 35c, the bandpass filter 36c and the photodetector 37c are optically coupled with each other. The dichroic mirror 35c is also optically coupled with the total reflection mirror 20 and the dichroic mirror 35d. The dichroic mirror 35d, the bandpass filter 36d and the photodetector 37d are optically coupled to each other. The dichroic mirror 35d is also optically coupled with the dichroic mirror 35e. The dichroic mirror 35e, the bandpass filter 36e and the photodetector 37e are optically coupled to each other. Moreover, the photodetectors 37c to 37e are electrically connected to the processing section 4.

The dichroic mirror 35c transmits light with wavelengths not less than 565 nm and reflects light with wavelengths less than 565 nm. The dichroic mirror 35d transmits light with wavelengths not less than 500 nm and reflects light with wavelengths less than 500 nm. The dichroic mirror 35e transmits light with wavelengths not less than 565 nm and reflects light with wavelengths less than 565 nm. The bandpass filters 36c to 36e have the wavelength regions $\lambda_{em1}$ to $\lambda_{em3}$ as the transmission regions thereof, respectively. Consequently, in the fluorescence traveling from the total reflection mirror 20 to the detector section 3b, the component in the wavelength region $\lambda_{em1}$ enters the photodetector 37d, the component in the wavelength region $\lambda_{em2}$ enters the photodetector 37e, and the component in the wavelength region $\lambda_{em3}$ enters the photodetector 37c. Instead of the dichroic mirror 35e, a total reflection mirror may be used.

The photodetectors 37c to 37e may be imaging devices such as cooled CCD cameras, or photomultipliers. The photodetectors 37c to 37e each generate output electric signals corresponding to the intensities of the incident fluorescence. The output signals are sent to the processing section 4.

Since the fluorescence from the specimen 5 is split into three beams of the wavelength regions $\lambda_{em1}$ to $\lambda_{em3}$ using the dichroic mirrors 35c to 35e and the bandpass filters 36c to 36e, the detector section 3b independently detects the fluorescence in these wavelength regions. Consequently, in the present embodiment, the FRET efficiency can also be measured by the procedures shown in. FIGS. 3 and 4.

The FRET analyzer 300 has the same advantages as the apparatuses of the above-described embodiments. Since the apparatus 300 has the detection wavelength region $\lambda_{em3}$, it is capable of measuring the fluorescence intensity of the acceptor during its bleaching in real time. Accordingly, the quantitative measurement of the FRET efficiency can be quickly performed by an easy operation. Moreover, by minimizing the time of illuminating the specimen 5 with the intense light for the bleaching to reduce the influences on the specimen 5, the FRET efficiency can be measured precisely.

Fourth Embodiment

A fourth embodiment of the present invention will now be described. An FRET analyzer of the fourth embodiment has the structure shown in FIG. 1, and performs an FRET analysis by the procedures shown in FIGS. 3 and 4. However, in the present embodiment, the method of determining the end of the monitoring of the acceptor bleaching at step S380 of FIG. 3 is different from that of the first to third embodiments. This difference will be described in the following:

In the present embodiment, the end time of the monitoring of the bleaching is obtained by calculation based on the fluorescence brightness of the acceptor measured during the monitoring of the bleaching. Generally, the fluorescence brightness of the acceptor attenuates exponentially with time during its bleaching. Therefore, the brightness I of the light detected by the CCD chip 24e during the monitoring of the bleaching is expressed as:

$$I = a \cdot e^{-bt} + c \quad (3),$$

where the first term $a \cdot e^{-bt}$ represents the fluorescence intensity of the acceptor, a and b are constants, and t is the elapsed time from the start of bleaching. The second term c represents the intensity of the light, other than the fluorescence of the acceptor, detected by the CCD chip 24e. Examples of such light include stray light produced in the FRET analyzer and self-fluorescence of the cells themselves of the specimen 5. When c is sufficiently low compared to the fluorescence intensity of the acceptor, the brightness I can be regarded as:

$$I = a \cdot e^{-bt} \quad (4).$$

It is considered that c is negligibly low compared to the fluorescence of the acceptor in the initial stage of the bleaching. Therefore, in the present embodiment, the fluorescence brightness is measured twice by the CCD chip 24e in the initial stage of the acceptor bleaching process. The constants a and b in the expression (3) are determined from the result of the measurement.

More specifically, at step S380, the processing section 4 obtains the EYFP fluorescent image at a time t0 at which a predetermined time has elapsed since the start of the bleaching. Further, the processing section 4 again obtains the EYFP fluorescent image at a time t1 at which a predetermined time has elapsed since the time t0. In order that c in the expression (3) can be ignored, these times t0 and t1 are set in the initial stage of the bleaching. Therefore, the brightness values $I_0$ and $I_1$ measured at the times t0 and t1 are expressed as:

$$I_0 = a \cdot e^{-bt0} \quad (5),$$

$$I_1 = a \cdot e^{-bt1} \quad (6).$$

The constants a and b can be calculated from these two expressions. This enables the fluorescence intensity of EYFP at a given time during the bleaching to be estimated based on the expression (4).

The processing section 4 uses the expression (4) to calculate the time when the value of the fluorescence intensity or the attenuation rate set at step S310 is obtained. At this step, the attenuation rate set at step S310 is treated as the attenuation rate of the fluorescence intensity from $I_0$, that is, $1-I/I_0$. The processing section 4 calculates, according to the expression (4), the time necessary to obtain the value that is set at step S310, and adds the calculated time to the start time of the monitoring of the bleaching to determine the end time of the monitoring. The processing section 4 stops the monitoring of the bleaching at the determined end time, and performs the processes of step S410 and succeeding steps.

The FRET analyzer of the this embodiment has not only the same advantages as those of the first embodiment but also the following advantage. In this embodiment, it is necessary to measure the fluorescence intensity of the acceptor only twice to determine the end time of the monitoring of the bleaching. Accordingly, the FRET efficiency can be measured more quickly.

However, according to the method of this embodiment, when c in the expression (3) is unignorably high, the precision of the determination of the bleaching monitoring end time is lowered. Moreover, there are cases where the expression (3) does not hold for some reason. In these cases, it is desirable to determine the end time of the monitoring of the bleaching by the method adopted in the first to third embodiments.

The method of determining the acceptor bleaching time adopted in this embodiment is also adoptable to the FRET analyzers having the structures shown in FIGS. 5 and 6.

The present invention has been described in detail with respect to the embodiments. However, the present invention is not limited to the above-described embodiments. The present invention may be modified in various manners without departing from the gist thereof.

In the above-described embodiments, ECFP and EYFP are used as the donor and acceptor pair. However, the present invention is applicable to other combinations of fluorescent dyes. Examples of such combinations include EGFP (donor) and RFP (acceptor), and EYFP (donor) and RFP (acceptor). When a combination of dyes different from that in the above embodiments is used, the same advantages as in the above embodiments can be obtained by setting the wavelength characteristics of the filter, the dichroic mirror or the prism according to the dyes.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A FRET (fluorescence resonance energy transfer) analyzer for measuring a FRET efficiency of a specimen containing a donor and an acceptor, the analyzer comprising:

an illuminator for selectively emitting light for donor excitation and light for acceptor bleaching;

a detector for detecting fluorescence emitted from the specimen in response to illuminating the specimen with the light for donor excitation, and generating an output corresponding to an intensity of the fluorescence; and a calculator for calculating the FRET efficiency using the output of the detector, the detector independently detecting light in first, second and third wavelength regions different from one another, the first wavelength region having a larger overlap with a fluorescence spectrum of the donor than with a fluorescence spectrum of the acceptor, the second wavelength region having a larger overlap with the fluorescence spectrum of the acceptor than with the fluorescence spectrum of the donor, and the third wavelength region having a larger overlap with the fluorescence spectrum of the acceptor than with the fluorescence spectrum of the donor, and having no substantial overlap with a wavelength region of the light for acceptor bleaching, the FRET analyzer further comprises a controller for controlling measurement of the FRET efficiency, the controller causing the illuminator to emit the light for donor excitation to cause fluorescence from the specimen, then causing the illuminator to emit the light for acceptor bleaching, determining whether the bleaching of the acceptor is completed according to an output in the third wavelength region of the detector, and when determining that the bleaching is completed, causing the illuminator to emit the light for donor excitation to cause fluorescence from the specimen.

2. A FRET analyzer according to claim 1, wherein the light for donor excitation has a wavelength region that overlaps with an absorption spectrum of the donor, and wherein the light for acceptor bleaching has a wavelength region that substantially does not overlap with the absorption spectrum of the donor and overlaps with an absorption spectrum of the acceptor.

3. A FRET analyzer according to claim 1, wherein the calculator calculates the FRET efficiency using an output in the first wavelength region of the detector before and after the bleaching by the following expression:

$$Et=1-Fd'/Fd,$$

where Et is a FRET efficiency, Fd' is a fluorescence intensity of the donor when FRET occurs, and Fd is a fluorescence intensity of the donor when no FRET occurs.

4. A FRET analyzer according to claim 1, further comprising an optical system disposed on an optical path between the illuminator and the detector, the optical system receiving light from the illuminator to send the received light to the specimen, receiving the fluorescence emitted from the specimen to send the received fluorescence to the detector, and preventing the light reflected at the specimen from the illuminator from entering the detector.

5. A FRET analyzer according to claim 4, wherein the optical system has a dichroic mirror switcher including a plurality of dichroic mirrors and selectively placing one of the dichroic mirrors on the optical path, and wherein the dichroic mirror placed on the optical path transmits the light from the illuminator to the specimen, transmits the fluorescence emitted from the specimen to the detector, and blocks the light reflected at the specimen from the illuminator.

6. A FRET analyzer according to claim 5, wherein the dichroic mirrors includes a first dichroic mirror for blocking the light for donor excitation and a second dichroic mirror for blocking the light for acceptor bleaching, and wherein the dichroic mirror switcher places the first dichroic mirror on the optical path when the light for donor excitation is emitted from the illuminator, and places the second dichroic mirror on the optical path when the light for acceptor bleaching is emitted from the illuminator.

7. A FRET analyzer according to claim 1, wherein the detector has a spectroscope with an incident surface and an exit surface, and first, second and third photodetectors optically coupled to the exit surface of the spectroscope, wherein the spectroscope receives the fluorescence from the specimen on the incident surface, disperses the received fluorescence in directions corresponding to wavelengths of the fluorescence, and sends components of the received fluorescence in the first, second and third wavelength regions from the exit surface to the first, second and third photodetectors, respectively, and wherein the first, second and third photodetectors generate outputs corresponding to intensities of the components in the first, second and third wavelength regions, respectively.

8. A FRET analyzer according to claim 1, wherein the detector has a filter switcher including first, second and third optical filters and selectively placing one of the optical filters on the optical path, and a photodetector optically coupled to the filter switcher, wherein the first, second and third filters placed on the optical path transmit light in the first, second and third wavelength regions, respectively, wherein the filter switcher receives the fluorescence from the specimen and sends component, extracted by the optical filter placed on the optical path, of the received fluorescence to the photodetector, and wherein the photodetector generates an output corresponding to an intensity of the component sent from the filter switcher.

9. A FRET analyzer according to claim 1, wherein the detector has:

an optical splitter for splitting the fluorescence from the specimen into three beams traveling on first, second and third optical paths;

first, second and third optical filters placed on the first, second and third optical paths, respectively; and first, second and third photodetectors for detecting light transmitting through the first, second and third optical filters to generate outputs corresponding to intensities of the detected light, wherein the first, second and third optical filters transmit the light in the first, second and third wavelength regions, respectively.

10. A FRET analyzer according to claim 1, wherein the illuminator has an optical attenuator adapted to place a light dimming filter on an optical path, wherein when the illuminator emits the light for donor excitation, the optical attenuator places the light dimming filter on the optical path so that the light for donor excitation passes through the light dimming filter, and wherein when the illuminator emits the light for acceptor bleaching, the optical attenuator removes the light dimming filter from the optical path so that the light for acceptor bleaching does not pass through the light dimming filter.

11. A FRET analyzer according to claim 10, wherein the third wavelength region has an overlap with the fluorescence spectrum of the acceptor so that fluorescence emitted from the acceptor when the specimen is illuminated by the light for acceptor bleaching is detected without saturation of the detector.

12. A FRET analyzer according to claim 1, wherein the illuminator has: a light source for emitting light in both a wavelength region of the light for donor excitation and a wavelength region of the light for acceptor bleaching;

an optical attenuator for receiving the light from the light source, the optical attenuator being adapted to place a light dimming filter on an optical path; and a wavelength selector for receiving the light from the optical attenuator to extract either component in the wavelength region of the light for donor excitation or the optical component in the wavelength region of the light for acceptor excitation, wherein when the illuminator emits the light for donor excitation, the optical attenuator places the light dimming filter on the optical path so that the light from the light source passes through the light dimming filter before entering the wavelength selector, and wherein when the illuminator emits the light for acceptor bleaching, the optical attenuator removes the light dimming filter from the optical path so that the light from the light source does not pass through the light dimming filter.

13. A FRET analyzer according to claim 12, wherein the third wavelength region has an overlap with the fluorescence spectrum of the acceptor so that fluorescence emitted from the acceptor when the specimen is illuminated by the light for acceptor bleaching is detected without saturation of the detector.

* * * * *